Figure 1:
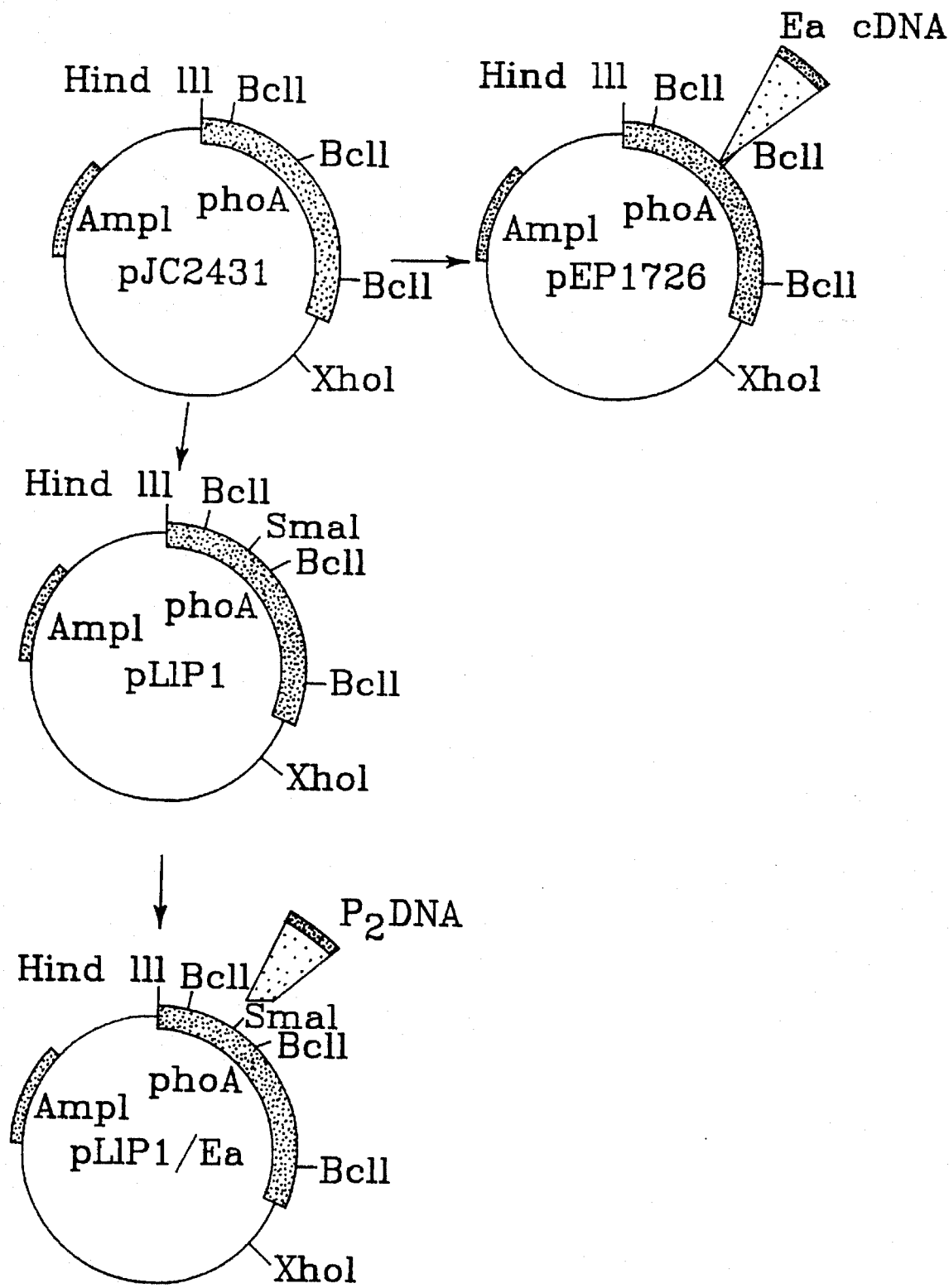
Figure 2:
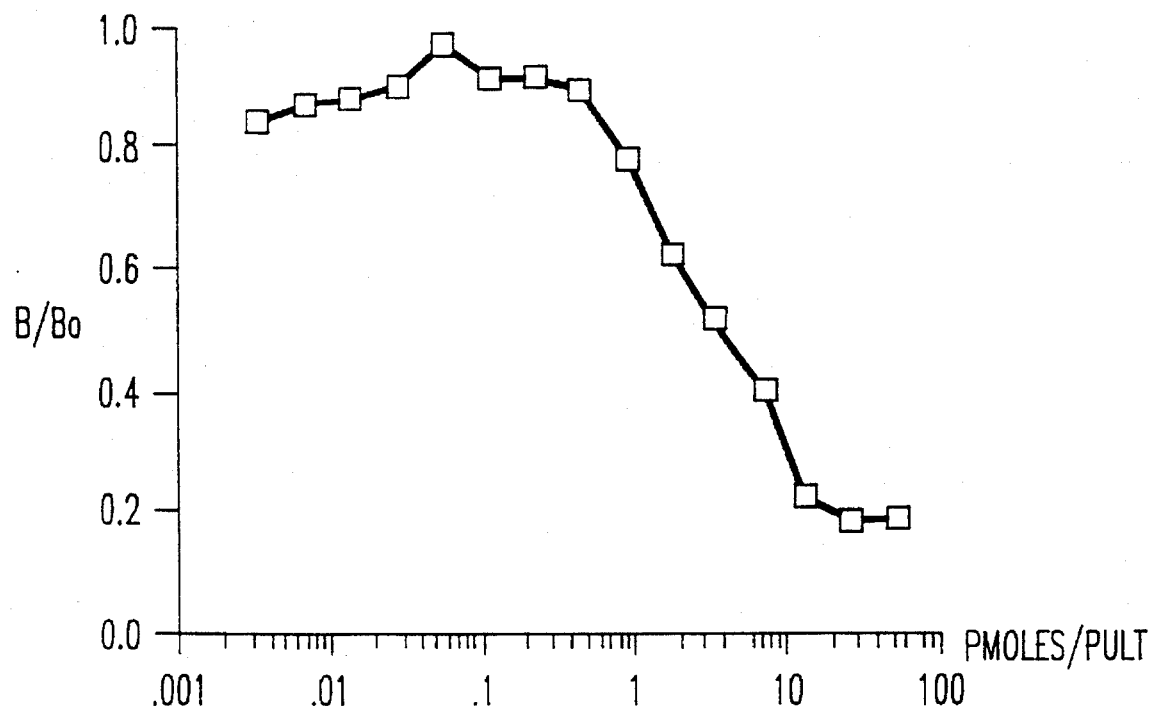

United States Patent [19]

Boquet et al.

[11] Patent Number: 5,534,223
[45] Date of Patent: Jul. 9, 1996

[54] HYBRID PROTEINS BETWEEN AN EXTRACYTOPLASMIC ENZYME AND AT LEAST ANOTHER PROTEIN, METHOD FOR PREPARING THEM AND ALSO THEIR APPLICATIONS

[75] Inventors: Paul Boquet, Marly le Roi; Jean-Claude Boulain, Palaiseau; Frederic Ducancel; Daniel Gillet, both of Paris; André Ménez, St Rémy les Cheurieuse, all of France

[73] Assignee: Commissariat a l'Energie Atomique, Paris, France

[21] Appl. No.: 269,072

[22] Filed: Jun. 30, 1994

Related U.S. Application Data

[63] Continuation of Ser. No. 876,910, Apr. 30, 1992, Pat. No. 5,362,644, which is a continuation of Ser. No. 542,772, Jun. 25, 1990, abandoned.

[30] Foreign Application Priority Data

Jun. 26, 1989 [FR] France .................................. 89 08444

[51] Int. Cl.⁶ .................................................. G01N 33/531
[52] U.S. Cl. .......................... 422/61; 435/7.9; 435/7.92; 435/21; 435/975; 530/350; 530/387.1; 530/391.3; 530/399
[58] Field of Search .................................. 435/7.92, 7.32, 435/7.37, 21, 7.9, 975; 530/350, 387.1, 399, 391.3; 422/61

[56] References Cited

U.S. PATENT DOCUMENTS 4,325,832  4/1982  Louderback ............................. 252/408
4,411,994  10/1983  Gilbert et al. ............................. 435/7.1
4,769,327  9/1988  Stephens et al. ........................... 435/68
4,774,175  9/1988  Chang et al. ................................ 435/5
5,011,772  4/1991  Recsei et al. ............................. 435/69.1

FOREIGN PATENT DOCUMENTS 8606742  11/1986  WIPO.

OTHER PUBLICATIONS

Huston, J. S. et al. "Protein Engineering of antibody binding sites . . . " Proceedings of the National Academy of Sciences, USA, 85:5879–5883, 1988.
Tamiya, T. et al. "Cloning and sequence analysis . . . " Biochimie 67:185–189, 1985.
Kunapuei, S. P. et al. "Expression of Human Agiotensin . . . " J. Biol. Chem. 262 (16) 7672–75, 1987.
Duncancel et al. "Recombinant Colorimetric . . . " Bio/Technology 11:601–605, 1993.

Primary Examiner—Christine M. Nucker
Assistant Examiner—Jeffrey Stucker
Attorney, Agent, or Firm—Oblon, Spivak, McClelland, Maier & Neustadt

[57] ABSTRACT

A kit for carrying out an immunoenzymological assay for protein, containing a diagnostic reagent consisting of a hybrid protein comprising, in order, a polypeptide P1 which is an N-terminal portion of mature alkaline phosphatase comprising from 6 to 28 of the N-terminal amino acids of said mature alkaline phosphatase, joined to a polypeptide P2, capable of interacting with an antibody or antigen joined to a polypeptide P3 which is selected from the group consisting of a) the C-terminal remaining amino acids of said mature alkaline phosphatase, b) the mature sequence of alkaline phosphatase, and c) enzymatically active fragments of b).

4 Claims, 2 Drawing Sheets

HYBRID PROTEINS BETWEEN AN EXTRACYTOPLASMIC ENZYME AND AT LEAST ANOTHER PROTEIN, METHOD FOR PREPARING THEM AND ALSO THEIR APPLICATIONS

This application is a continuation of Ser. No. 07/876,910 filed Apr. 30, 1992, now U.S. Pat. No. 5,362,644, which is a continuation of application Ser. No. 07/542,772 filed Jun. 25, 1990, now abandoned.

The present invention relates to hybrid proteins between a fragment of an extracytoplasmic protein P1, a protein P2 and an extracytoplasmic enzyme, the protein P2 being, in particular, an antigen or a single-chain variable fragment (Fv) of an antibody, to a method for preparing them and also to their applications, in particular, as a diagnostic agent and in the screening of a nucleic acid library or in the selection of recombinant clones.

The present invention also relates to the DNA sequences coding for said hybrid proteins, to expression vectors containing said sequences, to strains of bacteria or of yeasts transformed by said vectors and also to their application for the production and secretion of said hybrid proteins.

In the literature, a number of hybrid proteins have been described, as well as a method for preparing them.

There may be mentioned, in particular, U.S. Pat. Nos. 4,411,994 and 4,338,397, which describe the use of the penicillinase gene in plasmid pBR322 to produce fusion proteins, which are transported to the periplasmic space by the penicillinase "leader" sequence, using cDNA sequences coding for preproinsulin inserted at the PstI site of plasmid pBR322.

There may also be mentioned European Patent Application 196,864, which describes the use of the alkaline phosphatase "leader" sequence followed, downstream and in the reading frame, by the sequence coding for the desired protein.

The system for expression of said sequence includes a suitable promoter (for example the promoter of gene phoA), linked operationally to said hybrid coding sequence and, downstream from said sequence, a suitable terminator, in particular the phoA terminator.

This European Patent Application 196,864 discloses that only so-called susceptible proteins can be fused to the N-terminal portion of alkaline phosphatase and exported; it is, in addition, stated that a protein is considered to be susceptible when it contains an amino acid sequence which interacts with the alkaline phosphatase leader sequence and gives rise to the secretion of said sequence.

It is also stated that the susceptibility of the protein, doubtless due to the nature of its amino acid sequence which permits this interaction between the two sequences, is not at present understood. It is, however, clear that some heterologous proteins are capable of interacting with the signal sequence derived from a number of bacterial "leaders", whereas other proteins are incapable of this interaction.

This European application describes, more especially, hGH and TNF as susceptible proteins, whereas IL-2 is considered to be an insusceptible protein, that is to say not exported. The hybrid proteins described in this application are designed to produce, in particular, hGH or TNF in industrial quantities by a genetic recombination method, the alkaline phosphatase signal sequence serving exclusively for transport of the foreign protein.

European Patent Application 242,243 describes a hybrid protein comprising an enzyme containing an epitope, inserted in such a way into the peptide chain of the enzyme that the epitope is exposed so that, when the hybrid protein is in immunological contact with antibodies directed towards the epitope, a complex is formed between said hybrid protein and said antibodies and the enzymatic activity of said enzyme is preserved whether in the uncomplexed state or in the complexed state. The hybrid protein described in this European application is tucked into the outer membrane of a bacterium in such a way that the chosen epitope is exposed at the surface of the bacterium; E. coli strains carrying at their outer surface modified phage lambda receptors containing the hybrid proteins defined above exposed at the surface are also described in this application. The hybrid proteins described in this application can, where appropriate, comprise alkaline phosphatase, peroxidase or β-galactosidase.

There are other documents which describe fusion proteins enabling the desired secreted or exported product to be obtained. There may be mentioned especially the paper in the name of T. P. HOPP et al., published in Biotechnol., 1988, 6, 1204–1210, which describes a short N-terminal fusion sequence used as a marker for the identification and purification of recombinant proteins; the removal of said marker has the advantage of not necessitating drastic treatments of the fusion protein. It should be noted that, in this paper, T. P. HOPP et al. state that the production of fusion proteins has a number of drawbacks at the present time; in effect, it is not an obvious matter to obtain fusion proteins which possess a quaternary structure which corresponds to that of the native protein, which are stable and which retain the biological activity of the latter; there may also be mentioned the paper published in Biochemical and Biophysical Research, 1987, 149, 2, 607–614, which describes a hybrid protein which comprises successively proinsulin or a fragment of the latter and alkaline phosphatase and is obtained from a DNA comprising successively the proinsulin gene and the alkaline phosphatase gene (binding via the 5' end of the gene coding for mature phoA).

However, the descriptions of fused and/or exported proteins described in the literature apply only to special cases and cannot be capable of generalization.

The Applicant has accordingly aimed to provide a family of hybrid proteins directly exported in the periplasmic space or secreted out of the cell in their hybrid forms and consisting of a fragment of a protein P1, a protein P2 and an enzyme, said hybrid proteins retaining the properties of the protein P2 and of the enzyme and being capable of being used as a reagent for diagnosis and/or detection in the context of assays of the RA (receptor assay) or EIA (enzyme immunoassay) type, especially of the ELISA type, and for the selection of recombinant clones or for the screening of a DNA library; such hybrid proteins meet practical needs better than the hybrid proteins of the prior art, in particular in that said exported or secreted hybrid proteins are directly usable as a diagnostic reagent without a purification step, and are stable.

In addition, such hybrid proteins make possible, in particular, the assay of small molecules, which usually, even if they can be coupled chemically to an enzyme, are unable to find application as a reagent, and which have hitherto been essentially assayed by RIA.

It is also an object of the invention to provide the tools for the production of said hybrid proteins.

The subject of the present invention is a nucleic acid sequence, which consists of a hybrid sequence comprising successively the leader sequence of the structural gene for a suitable protein P1 exported or secreted by a microorganism, in particular chosen from the group which comprises bacteria and yeasts, a nucleic acid sequence coding for a $NH_2$-terminal fragment of said mature protein P1, a nucleic acid sequence coding for a protein P2 and then a fragment coding for at least one functional fragment of the mature sequence of a suitable extracytoplasmic enzyme, the assembly of these fragments being in a single reading frame and coding for a hybrid protein possessing simultaneously the properties of the enzyme and some properties of said protein P2, in particular that of interacting specifically with an antibody, an antigen or a receptor.

In the sense of the present invention, nucleic acid is understood to mean either a single-stranded or a double-stranded nucleic acid sequence, the nucleic acid being either a DNA or an RNA.

According to another advantageous embodiment of the sequence according to the invention, the enzyme is chosen from the group which comprises, in particular, alkaline phosphatase, acid phosphatase, acid glucose phosphatase, cyclic phosphodiesterase and β-lactamase.

According to another advantageous embodiment of the sequence according to the invention, the fragment of sequence coding for the protein P2 is, in particular, chosen from the group which comprises the sequences coding for peptide hormones, the sequences coding for a toxin and the sequences coding for a single-chain fragment analogous to the variable domains of immunoglobulins (recombinant immunoglobulins).

These latter fragments are, in particular, described in Proc. Natl. Acad. Sci. U.S.A., 1988, 85, 5879–5883.

According to an arrangement of this embodiment, the toxin is advantageously a neurotoxin.

According to the invention, the protein P1 is identical to or different from the enzyme defined above.

According to another advantageous embodiment of the sequence according to the invention, said nucleic acid sequence consists of a hybrid sequence comprising successively the leader fragment of the structural gene of an enzyme exported or secreted by a microorganism, in particular chosen from the group which comprises bacteria and yeasts, a nucleic acid sequence coding for a NH$_2$-terminal fragment of said mature enzyme, a nucleic acid sequence coding for a protein P2 and then a fragment coding for at least one functional fragment of the mature sequence of said enzyme, the assembly of these fragments being in a single reading frame and coding for a hybrid protein possessing simultaneously the properties of the enzyme and some properties of said protein, in particular that of interacting specifically with an antibody, an antigen or a receptor.

According to an advantageous arrangement of this embodiment, said hybrid sequence comprises successively the leader sequence of the structural gene for alkaline phosphatase, a fragment coding for, at most, the 28 N-terminal amino acids of mature alkaline phosphatase, a DNA sequence coding for a protein P2 or a fragment of the latter, and then a fragment coding for, at least, the 422 C-terminal remaining amino acids of alkaline phosphatase, the assembly of these fragments being in a single reading frame and forming a hybrid DNA sequence coding for a hybrid protein possessing simultaneously the properties of alkaline phosphatase, especially its enzymatic activity, and some of the properties of the protein P2, in particular that of interacting specifically with an antigen, an antibody or a receptor.

According to an advantageous variant of this arrangement, said hybrid DNA sequence comprises successively the nucleic acid sequence coding for the alkaline phosphatase leader peptide, the sequence coding for the 28 N-terminal amino acids of alkaline phosphatase, the sequence coding for mature erabutoxin a (ea) and the sequence coding for the 422 C-terminal amino acids of alkaline phosphatase.

According to this variant, the sequence coding for erabutoxin a comprises 192 base pairs and two additional Sau3AI restriction sites.

Said hybrid sequence comprises the formula I below:

```
                                                                    R   T   P
Leader fragment of the structural gene for phoA-                   CGG ACA CCA E   M   P   V   L   E   N   R   A   A   Q   G   D   I   T
GAA ATG CCT GTT CTG GAA AAC CGG GCT GCT CAG GGC GAT ATT ACT A   P   G   G   A   R   L   T   G  ↓Q   P   R   I   C
GCA CCC GGC GGT GCT CGC CGT TTA ACG GGT GAT CCC AGG ATA TGT F   N   H   Q   S   S   Q   P   Q   T   T   K   T   C   S
TTT AAC CAT CAG TCA TCG CAA CCG CAA ACC ACT AAA ACT TGT TCA P   G   E   S   S   C   Y   N   K   Q   W   S   D   F   R
CCT GGG GAG AGC TCT TGC TAT AAC AAG CAA TGG AGC GAT TTC CGT G   T   I   I   E   R   G   C   G   C   P   T   V   K   P
GGA ACT ATA ATT GAA AGG GGA TGT GGT TGC CCC ACA GTG AAG CCC G   I   K   L   S   C   C   E   S   E   V   C   N   N  ↓D
GGT ATT AAA CTC AGT TGT TGC GAA TCA GAG GTC TGC AAC AAT GAT Q   T
CAG ACT-fragment
``` coding for at least the 422 C-terminal remaining amino acids of alkaline phosphatase and is designated ea/phoA28.

The first arrow corresponds to the beginning of the insert containing erabutoxin a; the second arrow corresponds to the end of said insert.

The complete sequence of the structural gene for alkaline phosphatase (phoA gene) is described in GENE, 1986, 44, 121–125.

According to another advantageous arrangement of this embodiment, the hybrid nucleic acid sequence according to the invention comprises successively the leader sequence of the structural gene for alkaline phosphatase, a fragment coding for the 6 N-terminal amino acids of mature alkaline phosphatase, a nucleic acid sequence coding for a protein P2 or a fragment of the latter, and then a fragment coding for the 444 C-terminal remaining amino acids of alkaline phosphatase, which sequence comprises, in addition, in particular in order to place the assembly of these fragments in a single reading frame, downstream and/or upstream from the fragment coding for the protein P2, a suitable nucleic acid fragment, which hybrid sequence, in a single reading frame, codes for a hybrid protein possessing simultaneously the properties of alkaline phosphatase and some of the properties of the protein different from the enzyme, in particular that of interacting specifically with an antigen, an antibody or a receptor.

A hybrid nucleic acid sequence according to the invention, in which the sequence coding for the protein P2 is inserted after the triplet coding for the 6th amino acid of mature alkaline phosphatase, is, in particular, prepared by means of the insertion of at least one unique restriction site in the sequence coding for alkaline phosphatase, shifting the reading frame of the phoA gene out of phase and preventing expression of the alkaline phosphatase, whereas insertion of the protein P2 at said site enables, under the conditions of the invention, the alkaline phosphatase gene to be shifted back into phase and the enzyme to be expressed.

According to an advantageous variant of this arrangement, said hybrid DNA sequence comprises successively the leader sequence of the structural gene for alkaline phosphatase, the sequence coding for the 6 N-terminal amino acids of alkaline phosphatase, the nucleic acid sequence coding for angiotensin I, a fragment comprising the sequence AGG G and which enables the alkaline phosphatase gene to be shifted back into phase, and then a fragment coding for, at least, the 444 C-terminal remaining amino acids of alkaline phosphatase.

Said hybrid sequence comprises the formula II below:

of mature alkaline phosphatase. The underlined sequence is that of angiotensin I. The arginine preceding the valine +7 has been introduced on account of the needs of cloning and shifting of the phoA gene back into phase. The nucleotides corresponding to the unique restriction site defined above introduced into the phosphatase gene are shown in lowercase letters; these correspond, in the present case, to an SmaI site (ccc . . . ggg). This makes it possible to demonstrate the shifting of the phoA gene out of phase, caused by the presence of said site, and the shifting back into phase brought about by the introduction of the angiotensin sequence. The portion of phosphatase sequence not shown (dotted) corresponds to that published by CHANG et al. (CHANG, C. N., W.-J. KUANG, and E. Y. CHEN, 1986, Gene, 44:121–125).

According to another advantageous variant of this arrangement, said hybrid DNA sequence comprises successively the leader sequence of the structural gene for alkaline phosphatase, the sequence coding for the 6 N-terminal amino acids of alkaline phosphatase, a fragment comprising the sequence GAT CCC, the nucleic acid sequence coding for erabutoxin a, a fragment comprising the sequence GAT C, which fragment enables the alkaline phosphatase gene to be shifted back into phase, and then a fragment coding for,

```
-21
GTG AAA CAA AGC ACT ATT GCA CTG GCA CTC TTA CCG TTA CTG
Met lys gln ser thr ile ala leu ala leu leu pro leu leu -1  +1                      +6
TTT ACC CCT GTG ACA AAA GCC CGG ACA CCA GAA ATG ccc GAT
phe thr pro val thr lys ala arg thr pro glu met pro asp +7
CTG GTC TAT ATT CAC CCG TTT CAC CTT Agg gTT CTG GAA AAC
arg val tyr ile his pro phe his leu arg val leu glu asn CGG GCT GCT CAG GGC GAT ATT ACT GCA CCC GGC GGT GCT CGC
arg ala ala gln gly asp ile thr ala pro gly gly ala arg CGT TTA ACG . . .
arg leu thr . . .

.
.         +450
. . . CTG AAA TAA
. . . leu lys stop
```

This sequence of formula II is designated Angio/phoA6.

In this formula II, the negative numbering corresponds to the amino acids of the alkaline phosphatase signal peptide and the positive numbering corresponds to the amino acids at least, the 444 C-terminal remaining amino acids of alkaline phosphatase.

Said hybrid sequence comprises the formula III below:

```
-21                                                                        (III)
GTG AAA CAA AGC ACT ATT GCA CTG GCA CTC TTA CCG TTA CTG
Met lys gln ser thr ile ala leu ala leu leu pro leu leu -1  +1                      +6
TTT ACC CCT GTG ACA AAA GCC CGG ACA CCA GAA ATG ccc GAT
phe thr pro val thr lys ala arg thr pro glu met pro asp CCC AGG ATA TGT TTT AAC CAT CAG TCA TCG CAA CCG CAA ACC
pro arg ils cys phe asn his gln ser ser gln pro gln thr ACT AAA ACT TGT TCA CCT GGG GAG AGC TCT TGC TAT AAC AAG
thr lys thr cys ser pro gly glu ser ser cys tyr asn lys CAA TGG AGC GAT TTC CGT GGA ACT ATA ATT GAA AGG GGA TGT
gln trp ser asp phe arg gly thr ile ile glu arg gly cys GGT TGC CCC ACA GTG AAG CCC GGT ATT AAA CTC AGT TGT TGC
gly cys pro thr val lys pro gly ile lys leu ser cys cys
```

```
                                                   +7
GAA TCA GAG GTC TGC AAC AAT GAT Cgg gTT CTG GAA AAC CGG
glu ser glu val cys asn asn asp arg val leu glu asn arg GCT GCT CAG GGC GAT ATT ACT GCA CCC GGC GGT GCT CGC CGT
ala ala gln gly asp ile thr ala pro gly gly ala arg arg TTA ACG GGT GAT CAG ACT GCC ...
leu thr gly asp gln thr ala ...

.
.
.       +450
... CTG AAA TAA
... leu lys stop
```

This sequence of formula III is designated ea/phoA6.

In this formula III, the negative numbering corresponds to the amino acids of the alkaline phosphatase signal peptide and the positive numbering corresponds to the amino acids of mature alkaline phosphatase. The underlined sequence is that of erabutoxin a. The amino acids Asp-Pro and Asp-Arg on either side of the erabutoxin sequence have been introduced on account of the needs of cloning and shifting of the phoA gene back into phase. The nucleotides corresponding to the SmaI restriction site introduced into the phosphatase gene are shown in lower-case letters (ccc ... ggg). This makes it possible to demonstrate the shifting of the phoA gene out of phase, caused by the presence of said site, and the shifting back into phase brought about by the introduction of the erabutoxin sequence. The portion of phosphatase sequence not shown (dotted) corresponds to that published by CHANG et al. (CHANG, C. N., W.-J. KUANG, and E. Y. CHEN, 1986, Gene 44:121–125).

The subject of the present invention is also a protein, which consists of a hybrid sequence comprising successively a fragment of a protein P1 exported or secreted by a microorganism, in particular chosen from the group which comprises bacteria and yeasts, a suitable protein P2 or a fragment of the latter and at least one functional fragment of a suitable enzyme, said hybrid protein possessing simultaneously the properties of the enzyme and some properties of the protein P2, in particular of interacting specifically with an antibody, an antigen or a receptor.

According to an advantageous embodiment of said hybrid protein, the protein P1 is different from the enzyme.

According to another advantageous embodiment of said hybrid protein, the protein P1 is identical to the enzyme.

According to an advantageous arrangement of this embodiment, the said hybrid protein comprises an enzyme exported or secreted by a microorganism, in particular chosen from the group which comprises bacteria and yeasts, into which a suitable protein P2 is inserted.

According to another advantageous arrangement of this embodiment, said hybrid protein comprises successively a fragment of an enzyme exported or secreted by a microorganism, in particular chosen from the group which comprises bacteria and yeasts, a suitable protein P2 and then the complete mature sequence of said enzyme.

According to another advantageous embodiment of the hybrid protein according to the invention, it contains a protein P2, in particular chosen from the group which comprises peptide hormones, single-chain fragments analogous to the variable fragments of immunoglobulins and toxins, inserted into an enzyme chosen from the group which comprises, in particular, alkaline phosphatase, acid phosphatase, acid glucose phosphatase, cyclic phosphodiesterase and β-lactamase.

According to an arrangement of this embodiment, said hybrid protein advantageously comprises a neurotoxin inserted into alkaline phosphatase.

According to an advantageous variant of this arrangement, the neurotoxin is erabutoxin a (ea), which hybrid protein possesses the sequence deduced according to the formula I or III above.

According to another arrangement of this embodiment, said hybrid protein advantageously comprises angiotensin I inserted into alkaline phosphatase, and possesses the sequence deduced according to the formula II above.

The present invention has, in particular, the advantage of expressing, unexpectedly, both an enzyme and a functional protein P2, whether it is inserted into the enzyme or sandwiched between a protein P1 and said enzyme, and of possessing great stability. It also has the advantage of expressing a small functional protein which, hitherto, even if it could be coupled chemically with an enzyme, could not find application as a reagent and, accordingly, could not be used in assays of EIA or ELISA type, but only in assays of the RIA type, which are much more awkward to carry out.

The subject of the present invention is also a family of vectors for the expression and/or cloning of a hybrid protein according to the invention, wherein each vector includes an expression system comprising:

a suitable promoter, a ribosome-binding site, a nucleic acid sequence containing the leader sequence of the structural gene for a protein P1, a sequence coding for a $NH_2$-terminal fragment of said mature protein P1, a sequence coding for a protein P2 inserted at a natural restriction site and the mature sequence coding for an enzyme or a fragment of the latter, which nucleic acid sequence corresponds to a hybrid sequence according to the invention, and a transcription terminator, which expression system is inserted into a suitable genetic structure, in particular chosen from the group which comprises plasmids, phages, cosmids or suitable chromosomes.

According to an advantageous embodiment of said vector, the genetic structure is a plasmid and the protein P1 is identical to the enzyme.

According to an advantageous arrangement of this vector, when P2 is advantageously erabutoxin a, a plasmid is obtained possessing the following properties:

it comprises 6.1 kb;

it is obtained by ligation of plasmid pJC2431 carrying the structural gene for alkaline phosphatase and the gene for resistance to ampicillin ($Ap^R$)—said plasmid being linearized at the site BclI, at codon 28 of said structural gene for alkaline phosphatase—with the 192-base pair Sau3AI-Sau3AI fragment coding for erabutoxin a.

This plasmid has been designated pEP1726 by the inventors.

Plasmid pJC2431 is described in the paper by J. C. LAZZARONI et al., published in J. Bacteriol., 1985, 164, 1376–1380.

The subject of the present invention is also another family of vectors for the expression and/or cloning of a hybrid protein according to the invention, wherein each vector includes an expression system comprising:

a suitable promoter, a ribosome-binding site, a nucleic acid sequence containing the leader sequence of the structural gene for a protein P1, a sequence coding for a NH$_2$-terminal fragment of said mature protein P1, the sequence coding for an extracytoplasmic enzyme or a fragment of the latter and one or more unique restriction sites, capable of receiving a sequence coding for a protein P2, situated at the junction between the fragment of sequence coding for the protein P1 and the sequence coding for the enzyme, and a transcription terminator, which expression system is inserted into a suitable genetic structure, in particular chosen from the group which comprises plasmids, phages, cosmids or suitable chromosomes.

According to an advantageous embodiment of the said vector, at least one of the unique restriction sites introduced causes a shifting of the gene for the enzyme out of phase, the shifting of said gene back into phase being effected by the introduction of the sequence for the protein P2.

According to an advantageous arrangement of this embodiment, a plasmid is obtained possessing the following properties:

it comprises approximately 5.9 kb, and it is obtained by directed mutagenesis of the phoA gene carried by plasmid pJC2431, so as to introduce a unique SmaI restriction site corresponding to position +6 of the mature protein.

Such a plasmid has been designated pLIP1 by the inventors and is said to be unladen.

When the sequence coding for the protein P2 is inserted at a restriction site naturally present in the structural gene for phoA, or when the sequence coding for the protein P2 is inserted at a unique restriction site introduced beforehand into the structural gene for phoA, such vectors contain hybrid sequences according to the invention and directly express the hybrid protein when they are present in a suitable microorganism; such vectors are said to be loaded, whereas the vector designated pLIP1, capable of receiving a protein P2, is, for its part, said to be unladen.

The subject of the present invention is also a microorganism obtained by genetic transformation, which is obtained by suitable modification of a suitable strain of E. coli with a vector according to the invention, and in particular by transformation when said vector is a plasmid.

According to an embodiment of the invention, said microorganism is advantageously an E. coli strain CC118 transformed by plasmid pEP1726.

Such a strain transformed by said plasmid was deposited on the date 2 Jun. 1989 under number I-862 with the Collection Nationale des Cultures de Microorganismes [National Collection of Microorganism Cultures] held by the Pasteur Institute.

Said strain is designated SEP 1726 by the inventors.

According to another embodiment of the invention, said microorganism is advantageously an E. coli strain CC118 transformed by plasmid pLIP1.

Such a strain transformed by said plasmid was deposited on the date 7 Jun. 1990 under number I-954 with the Collection Nationale des Cultures de Microorganismes [National Collection of Microorganism Cultures] held by the Pasteur Institute.

Such an unladen vector has the advantage of enabling any sequence coding for a protein to be inserted at this unique restriction site.

This modification of the structural gene for alkaline phosphatase introduces, in addition, a frameshift in the nucleotide sequence situated downstream, which sequence is characteristic of the functional portion of phoA.

This unladen vector, which corresponds to plasmid pLIP1 defined above, hence does not express alkaline phosphatase activity.

The formula IV below presents an alignment of the nucleotide and protein sequences corresponding to the native phoA gene (A), the modified phoA gene carried by the unladen vector pLIP1 (B) and the hybrid phoA gene carried by the loaded vector (C).

A. Native phosphatase:

```
CGG  ACA  CCA  GAA  ATG  CCT  GTT  CTG  GAA  AAC  CGG  GCT  GCT  CAG
arg  thr  pro  glu  met  pro  val  leu  glu  asn  arg  ala  ala  gln
+1                      +6   +7

....  CTG  AAA  TAA
....  leu  lys  stop
           +450
```

B. Introduction of the SmaI site (unladen vector pLIP1):

```
CGG  ACA  CCA  GAA  ATG  ccc  ggg  TTC  TGG  AAA  ACC  GGG  CTG  CTC
arg  thr  pro  glu  met  pro  gly  phe  trp  lys  thr  gly  leu  leu
+1                      +6

....  TTT  TGC  TGA
....  phe  cys  stop
           +49
```

C. Insertion and shifting back into phase enabling a phosphatase hybrid to be obtained (loaded vector):

```
                                                insert                                              (IV)
CGG  ACA  CCA  GAA  ATG  ccc  3n+1  gg  gTT  CTC  GAA  AAC  CGG  GCT
arg  thr  pro  glu  met  pro  xxx.x xx  val  leu  glu  asn  arg  ala
+1                        +6            +7

GCT  ...  CTG  AAA  TAA
ala  ...  leu  lys  stop
          +450
```

The nucleotides originating from the native phoA gene are shown in capital letters. The numbering corresponds to the amino acids of mature alkaline phosphatase. The dotted lanes correspond to the portions of sequences not shown. The nucleotides corresponding to the SmaI restriction site introduced into the phoA gene are shown in lower-case letters (cccggg) (B). The frameshift thereby introduced leads to the synthesis of an aberrant protein of 49 amino acids (B). The introduction at the SmaI site of a sequence of 3n+1 base pairs (insert) not containing the termination codon enables the phoA gene to be shifted back into phase and a hybrid protein to be obtained (C). Furthermore, if the 3n+1 sequence in its opposite orientation contains a termination codon, only the introduction of this sequence in the desired orientation will enable a protein possessing phosphatase activity to be obtained.

According to the invention, the promoter is chosen from the group which comprises the phoA gene promoter and any stronger promoter than the phoA gene promoter.

The phoA gene promoter, in particular, is an inducible promoter which is activated when the phosphate concentration in the culture medium of the bacteria becomes very low.

Such a promoter has, in particular, the advantage of enabling hybrid proteins to be produced in a phosphate-poor culture medium. The depletion of phosphate in the medium during the culture of the bacteria permits an induction of the synthesis of the hybrid proteins after the bacterial mass has increased. The advantage of such an inducible system is to reduce the risks of proteolysis during production, inasmuch as the proteins extracted are synthesized at the end of culturing. The homogeneity of the hybrid is thereby increased.

The subject of the present invention is also a process for the expression of a hybrid protein according to the invention, which employs an expression vector as defined above in a microorganism according to the invention.

Two properties of the hybrid protein must be emphasized:

(1) the extreme simplicity of its production and the absence of long and difficult purification steps;

(2) its stability during its production by bacteria, during its storage in different conditions and during the enzymatic test, since the enzymatic activity persists for more than 24 hours in the presence of the substrate.

The subject of the present invention is also a diagnostic reagent, which consists of a hybrid protein according to the invention.

Such a reagent finds, in particular, application in immunoenzymological assays, in the detection of receptors or as histochemical labels.

The subject of the present invention is also a method for the immunoenzymological assay of proteins, which consists in detecting proteins present in a biological fluid by bringing said biological fluid into contact with the diagnostic reagent according to the invention and wherein the presence of said reagent in the form of a complex or in free form is visualized by a suitable colorimetric reaction.

According to an advantageous embodiment of said method, said proteins are antigens.

According to another advantageous embodiment of said method, said proteins are antibodies.

The subject of the present invention is, furthermore, a ready-to-use kit for carrying out said immunoenzymological assay, which comprises, apart from the appropriate quantities of buffers and reagents useful for carrying out said assay, suitable quantities of the reagent according to the invention.

The reagent according to the invention has the advantage of being directly usable, whereas usually, in the context of an EIA or ELISA assay, the antigen or antibody is bound covalently to an enzyme, the coupling being carried out chemically. To be effective, such a coupling must be carried out using two highly purified components.

The subject of the present invention is also a method for screening libraries of cDNA or of genomic nucleic acid, or for the selection of recombinant clones, wherein the possible presence of an enzyme exported or secreted from clones of bacteria or of eukaryotic cells which have, where appropriate, integrated a plasmid, a phage, a cosmid or a recombinant chromosome under investigation containing a hybrid nucleic acid sequence according to the invention is visualized by a colorimetric reaction or a selection on a suitable culture medium.

According to an advantageous embodiment of said method, when the enzyme is alkaline phosphatase, the presence of the exported or secreted enzyme is visualized using a suitable substrate for said enzyme.

According to another advantageous embodiment of said method, when the enzyme is β-lactamase, the presence of the exported or secreted enzyme is visualized using a medium containing ampicillin.

In effect, an expression system containing, downstream from the inserted sequence for the protein P2, the gene specifying β-lactamase enables open reading frames to be cloned effectively and exclusively. These constructions lead to the synthesis of hybrid proteins containing the desired polypeptides followed by functional β-lactamase. The bacteria expressing such proteins are then selected by their resistance to ampicillin.

Apart from the foregoing arrangements, the invention also comprises other arrangements which will emerge from the description which follows, which refers to examples of implementation of the method which is the subject of the present invention.

It should nevertheless be clearly understood that these examples are given only by way of illustration of the subject of the invention and in no way constitute a limitation of the latter.

Example 1: Method of Production of Plasmid pEP1726.

Preparation of the Sau3AI-Sau3AI fragment coding for erabutoxin a: the 192-base pair Sau3AI-Sau3AI restriction fragment coding for erabutoxin without a signal sequence was prepared from the replicative form of the phage M13mp19 (−2 GAT, −1 CCC, +63 GAT) ea containing the Ea gene carrying mutations in respect of 3 codons, these modifications leading to the formation of two new Sau3AI restriction sites in the gene: −2 TAC (Tyr) becomes GAT (Asp); −1 ACC (Thr) becomes CCC (Pro); +63 TAG (AMB)

becomes GAT (Asp) (see formula I); this fragment is put in the presence of the vector pJC2431 opened by partial cleavage with BclI and DNA ligase. The ligations were performed in the buffer 50 mM Tris-HCl pH 7.4, 10 mM MgCl$_2$, 10 mM DTT, 0.5 mM ATP and 100 µg/ml BSA, with 1 U of phage T4 DNA ligase and a vector/insert concentration ratio of 1:10. Dephosphorylation of the vector was carried out according to Maniatis et al.

FIG. 1 shows plasmid pJC2431 carrying the structural gene for alkaline phosphatase under the control of its own promoter (Lazzaroni et al., 1985). This plasmid possesses three BclI restriction sites: BclI$^1$ situated upstream from the phoA promoter, and BclI$^2$ and BclI$^3$ situated, respectively, at codons +28 and +363 of the phoA gene; the insertion of ea into the site BclI$^2$ enables plasmid pEP1726, of interest for the production of a hybrid protein according to the invention, to be obtained.

Since the enzyme BclI cannot cut DNA at restriction sites methylated by dam-methylase, a dam-strain GM2163 is transformed with pJC2431 in order to prepare unmethylated plasmid. A partial digestion of pJC2431 with BclI and a dephosphorylation are then performed. The DNA corresponding to the opened plasmid (a single cut by BclI out of the three possible cuts) is then isolated on a low-melting point agarose gel according to the protocol of Maniatis et al. (1982).

Example 2: Expression of the Hybrid Protein ea/phoA28 (Insertion at aa28 of Alkaline Phosphatase).

The strain CC118 (ΔphoA20) was transformed with the ligation mixture described in Example 1. The Ap$^r$ (ampicillin-resistant) transformants obtained were purified on alkaline phosphatase-inducing medium containing XP and ampicillin.

The inducing medium is TES (solution of (NH$_4$)$_2$SO$_4$ 2 g/l, FeSO$_4$·7H$_2$O 0.5 mg/l, KCl 75 mg/l and triethanolamine 7.5 g/l, adjusted to pH 7.5). The addition of the chromogenic substrate 5-bromo-4-chloro-3-indolyl phosphate (XP 0.4 g/l) to this medium enables the alkaline phosphatase activity to be visualized on Petri dishes, the XP imparting a blue coloration to the colonies which hydrolyze it.

Three types of transformants have been distinguished according to their capacity to hydrolyze XP: colorless clones, blue clones and finally very deep blue clones. The latter two categories hence possess an alkaline phosphatase activity due to the plasmid which they contain.

Analysis of the restriction fragments of the plasmid DNA of these different transformants has enabled the site and orientation of the insertion of the ea gene to be determined in each case.

The deep blue clones correspond to insertions of one or two Sau3AI-Sau3AI fragments at the site BclI$^1$, that is to say upstream from the phoA gene and its promoter. The alkaline phosphatase activity of these clones is identical to that of the strain CC118 (pJC2431).

The less pronounced blue clones correspond to an in-frame insertion of a copy of the ea gene at the site BclI$^2$ (pEP1726).

The colorless clones originate from insertion of the ea gene at the site BclI$^2$, but in the opposite orientation to that of the phoA gene.

The protocol used for extraction of the periplasmic proteins by osmotic shock is that described by Dvorak et al. (1967).

Example 3: Method for Obtaining Plasmid pLIP1 (Unladen Expression Vector) and Plasmid pLIP1/P2 (Loaded Expression Vector).

1. Introduction of a Cloning Site into the phoA Gene.

The phoA gene (*E. coli* alkaline phosphatase) carried by plasmid pJC2431 was modified by directed mutagenesis in order to introduce a unique SmaI restriction site, after the codon corresponding to the sixth amino acid of the mature protein, and was chosen for two reasons:

the N-terminal region of the phosphatase can be modified without major impairment of its enzymatic activity, the presence of the first N-terminal amino acids is necessary in order to permit cleavage of the signal peptide.

This site was introduced so as to bring about a frameshift in the phoA gene. In consequence, this modified gene is incapable of expressing a functional protein.

2. Introduction of Exogenous DNA Sequences into the phoA Gene.

The DNA fragments intended for introduction into the phoA gene at the SmaI site are obtained by nucleotide synthesis or originate from cloned gene sequences. They are prepared so as to meet the following requirements:

(1) their 5' and 3' ends must be blunt, the SmaI site generating blunt ends;

(2) their introduction in the desired orientation must enable the phoA gene sequence downstream from the insertion site to be shifted back into phase and must permit the synthesis of a hybrid protein possessing phosphatase activity; and (3) their sequence in the orientation opposite to that desired must possess a termination codon in phase with the reading frame. This must bring about an absence of function of the hybrid gene obtained in the case of insertion in this orientation.

The gene constructions are obtained by the classical techniques of genetic engineering.

Only vectors which have inserted the exogenous sequences in the correct direction will have an open reading frame permitting the expression of a hybrid protein consisting of the polypeptide encoded by the inserted sequence and alkaline phosphatase.

3. Selection of the Hybrid Genes.

After ligation of the desired DNA fragment in the vector pLIP1, the recombinant plasmids are used to transform the bacterial strain CC118, an *E. coli* mutant not expressing alkaline phosphatase. Only the bacterial clones containing the expected gene construction will be capable of recovering a phosphatase activity. This activity may be visualized by culturing the bacteria on a suitable selection medium containing a chromogenic substrate for the phosphatase. The positive clones appear blue.

Thus, the appearance of the blue coloration, indicating that the bacterium expresses a protein possessing phosphatase activity, means:

that the exogenous DNA fragment has been inserted correctly, in the appropriate orientation, enabling the phosphatase coding sequence to be shifted back into phase, that the hybrid protein, a product of the recombinant gene, is correctly exported into the periplasm of the bacterium, that the hybrid protein produces dimers in order to form the homodimer corresponding to the active form of the phosphatase, and hence that the insertion of the exogenous protein sequence into the phosphatase does not greatly impair its enzymatic activity.

Example 4: Expression of the Hybrid Proteins ea/phoA6 and Angio/phoA6:

1. Introduction of a Protein P2 into Alkaline Phosphatase:
   This is carried out between amino acids 6 and 7 of the mature phosphatase. Said hybrid proteins consist of:
   - the 21 amino acids of the phosphatase signal peptide. This peptide enables the protein to be exported to the periplasmic space of the bacterium. This localization is essential for the acquisition of phosphatase activity and for a convenient extraction of the hybrid protein;
   - the 6 N-terminal amino acids of the phosphatase. Their presence permits cleavage of the signal peptide during the passage into the periplasm;
   - the amino acid sequence of the exogenous protein inserted into the phosphatase. The demands of cloning can, where appropriate, introduce one or more additional amino acids at the ends of this sequence; and
   - the last 444 amino acids of the phosphatase.

2. Production of the Hybrid Proteins:
   The bacteria are cultured in a phosphate-poor liquid medium. When the phosphate is exhausted, the phosphatase promoter is activated and leads to transcription of the hybrid gene. The advantage of this induction phenomenon is to permit a rapid synthesis of the hybrid proteins at the end of culturing (4 to 5 hours of culture), and hence to limit the risks of proteolytic degradation. The proteins of the bacterial periplasm are extracted by osmotic shock. The use of the protein hybrids (as reagents, for example) does not necessitate further purification.

3. Toxin/Phosphatase Hybrid (ea/phoA6).
   Gene construction:
   A 196-base pair fragment comprising the erabutoxin a coding sequence, flanked at the 5' and 3' ends by a Sau3AI site as specified above in Example 1, was repaired with Klenow polymerase and introduced at the SmaI site of plasmid pLIP1. The presence of a termination codon in phase, in the fragment in the opposite orientation, permitted a visual selection of the searched recombinant clones according to the principle described above in Example 2. The plasmid thereby obtained was designated pLIP1/ea. The expected polypeptide chain (ea/phoA6) comprises successively: the phosphatase signal peptide, the first 6 amino acids of the phosphatase, two additional amino acids introduced on account of the needs of cloning (Asp, Pro), the 62 amino acids of erabutoxin a, two additional amino acids introduced on account of the needs of cloning (Asp, Arg) and the last 444 amino acids of the phosphatase. The signal peptide is cleaved during the passage into the periplasm.
   Characteristics of the hybrid protein ea/phoA6:
   The hybrid protein ea/phoA6 was produced according to the procedure described above.
   Three characteristics of the hybrid were studied:
   (1) its enzymatic activity,
   (2) the presence of antigenic determinants specific to erabutoxin, and
   (3) the possibility of using the hybrid for performing an assay of free toxin.
   These characteristics were compared with those of the hybrid ea/phoA28 (Example 2), a product of plasmid pEP1726, obtained by the introduction of erabutoxin into the phosphatase after position 28 without prior modification of the phoA gene, using a pre-existing restriction site.
   a. The enzymatic activity of the hybrids was evaluated by comparison with that of native alkaline phosphatase obtained under the same conditions of production. The specific activity of bacterial periplasmic extracts, obtained by osmotic shock, containing the different proteins was determined. The protein concentration of the extract is determined from its absorbance at 465 nm and from a standard curve produced by protein assay by Bradford's method (Bradford, 1976). The enzymatic activity is measured on 20 μl of extract. After incubation for 15 min at 37° C. in the presence of 25 mM p-nitrophenyl phosphate (pNPP), the reaction is stopped by adding 1 ml of 1M NaOH. The absorbance of the sample is read at 410 nm (yellow coloration due to the formation of pNPOH). The specific enzyme activity (SA), in nmol of pNPP hydrolyzed per minute per mg of protein, is given by the formula:

$$SA = \frac{A410 \times 5.55}{(\text{mg protein/ml}) \times 2 \times 10^{-2}}$$

The measure of the activity of the hybrids is expressed as a percentage of specific activity corresponding to the native phosphatase.
   Native phosphatase: 100% (SA)
   ea/phoA6: 50%
   ea/pho28: 30%
   b. The presence of antigenic determinants specific to erabutoxin carried by the hybrid proteins ea/phoA6 and ea/phoA28 was studied by an ELISA test. These proteins are capable of binding to the monoclonal antibody Mα2-3, specific for an antigenic determinant carried by the native toxin. Furthermore, there is a competition for binding between ea/phoA or ea/phoA28and the native toxin. In order to evaluate the level of structuring of the toxin in the hybrids, we compared by an ELISA test its recognition by a serum directed towards the native toxin and by a serum directed towards the denatured toxin. To the extent of 60% of the hybrid ea/phoA6, the toxin is correctly structured, whereas this proportion is only 32% for the hybrid ea/phoA28.
   c. FIG. 2 illustrates an assay of erabutoxin a by an ELISA test using the hybrid ea/phoA6.
   The competition for binding between ea/phoA6 and the free toxin to the monoclonal antibody Mα2-3 was studied by an ELISA test. After adsorption of the antibody on an ELISA plate, ea/phoA6 (osmotic shock diluted 10-fold) is added in the presence of different quantities of toxin.

$$\text{The ratio } \frac{B}{Bo} = \frac{\text{quantity of hybrid bound in the presence of toxin}}{\text{quantity of hybrid bound in the absence of toxin}}$$

is expressed in terms of the quantity of free toxin. The sensitivity of this test, evaluated by the quantity of toxin for which the ratio B/Bo=0.5, is 2.5 pmol, equivalent to 17 ng. This sensitivity is equivalent to that of an RIA test using the tritiated toxin.

4. Angiotensin I/Phosphatase Hybrid (Angio/phoA6).
   Gene construction:
   A 31-base pair fragment capable of coding for angiotensin I was obtained by hybridization of two complementary synthetic oligonucleotides. This fragment was introduced at the SmaI site of plasmid pLIP1. The sequence of this fragment was determined so as to introduce a termination codon in phase with the reading frame of the phosphatase when its integration takes place in the orientation opposite to that desired. Thus, after the sequencing of several clones selected for the expression of a phosphatase activity (blue clones), they all corresponded to the desired construction. The plasmid thereby obtained was designated pLIP1/Angio. The expected polypeptide chain (Angio/phoA6) comprises successively: the phosphatase signal peptide, the first 6 amino acids of the phosphatase, the 10 amino acids of angiotensin I, an additional amino acid introduced on account of the needs of cloning (Arg) and the last 444 amino acids of the phosphatase. The signal peptide is cleaved during the passage into the periplasm.

Characteristics of the hybrid protein Angio/phoA6:

The hybrid protein Angio/phoA6 was produced according to the procedure described above.

Figure 3:
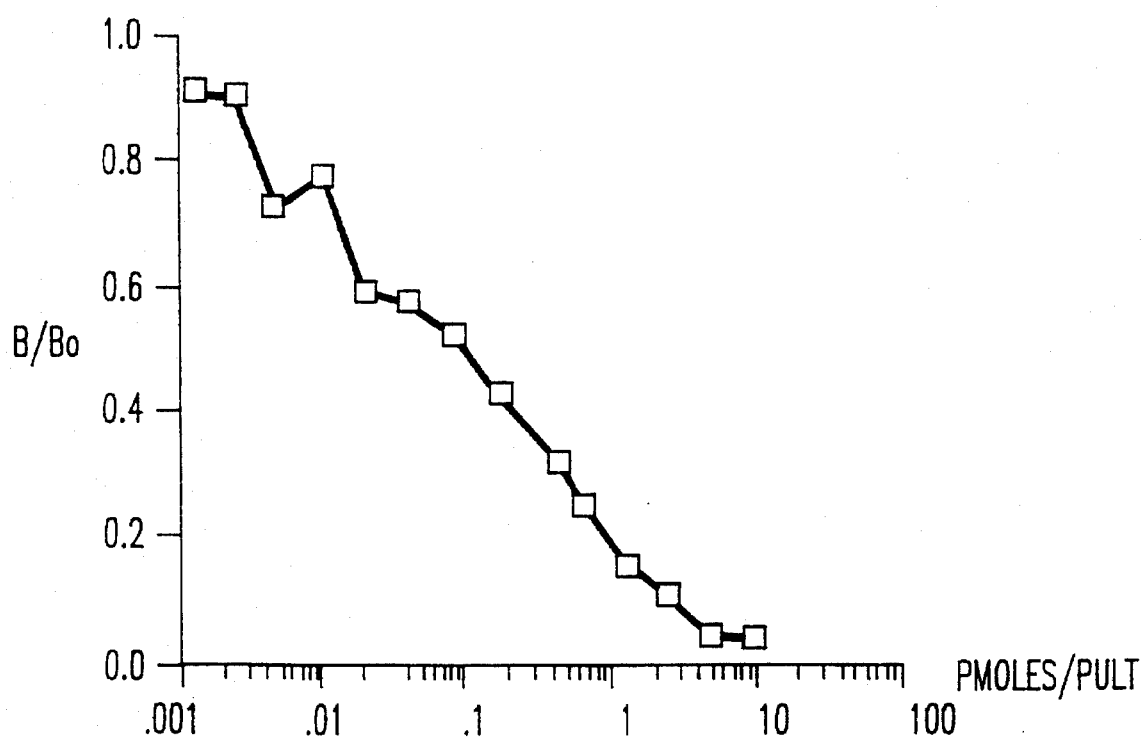

Three characteristics of the hybrid were studied:
(1) its enzymatic activity,
(2) its recognition by a serum directed towards angiotensin I, and
(3) the possibility of using the hybrid for performing a hormone assay.

a. The enzymatic activity of the hybrid Angio/phoA6 was evaluated according to the procedure described above for the hybrid ea/phoA6. This measure is expressed as a percentage of specific activity corresponding to the native phosphatase:
Native phosphatase: 100% (SA)
Angio/phoA6: 93% b. The recognition of the hybrid protein Angio/phoA6 by a serum directed towards angiotensin I was studied by an ELISA test. A pig serum directed towards rabbit immunoglobulins was adsorbed on an ELISA plate. A rabbit serum directed towards angiotensin I coupled to bovine serum albumin was then bound to the pig serum. Finally, the hybrid protein Angio/phoA6, produced by osmotic shock, was added to the system. Its binding to the antibodies directed towards angiotensin was visualized through its phosphatase activity by adding a chromogenic substrate for the enzyme. The specificity of this recognition is demonstrated by the existence of a competition for binding between the hybrid and free hormone.

c. FIG. 3 illustrates an assay of angiotensin I by an ELISA test using the hybrid Angio/phoA6.
The competition for binding between Angio/phoA6 and free angiotensin I to a rabbit serum directed towards this hormone was studied by an ELISA test. The rabbit serum is bound beforehand to a pig anti-rabbit immunoglobulin serum adsorbed on an ELISA plate. The hybrid Angio/phoA6 (osmotic shock diluted 20-fold) is added in the presence of different quantities of angiotensin I.

$$\text{The ratio } \frac{B}{Bo} = \frac{\text{quantity of hybrid bound in the presence of hormone}}{\text{quantity of hybrid bound in the absence of hormone}}$$

is expressed in terms of the quantity of free hormone. The sensitivity of this test, evaluated by the quantity of hormone for which the ratio B/Bo=0.5, is 0.09 pmol, equivalent to 0.12 ng. This sensitivity is equivalent to that of RIA tests used in common diagnostic practice (kit marketed by COMPAGNIE ORIS INDUSTRIE FRANCE).

Example 5: Stability of the Phosphatase Hybrid Proteins.

1. Induction of the Synthesis of the Phosphatase Hybrids:
In the expression vector produced, pLIP1, the phoA gene promoter has been retained in order to enable the hybrid genes to be expressed. This promoter is an inducible promoter which is activated when the phosphate concentration in the culture medium of the bacteria becomes very low.

Under the conditions chosen (see Example 4.2), the synthesis of the hybrid proteins, measured by the appearance of phosphatase activity, begins after 3 hours 30 minutes of culture. Extraction is carried out when the maximum accumulation of the hybrids is reached, namely after 4 hours 30 minutes to 5 hours.

2. Stability of the Hybrid Proteins:
The stability of the hybrid proteins was evaluated in three situations:
(1) stability during their production,
(2) stability during their use,
(3) stability during storage operations.

a. The stability of the hybrids and of the native phosphatase was studied by visualizing their integrity after labeling with [$^{35}$S]methionine, immunoprecipitation and polyacrylamide gel electrophoresis. The bacteria are cultured under the usual conditions of production. Labeling of the hybrids with [$^{35}$S]methionine is carried out at the time of induction of their synthesis for 30 minutes. The proteins immunoprecipitated with a monoclonal antibody specific for alkaline phosphatase appear in the form of a single molecular species. The molecular masses observed are very close to the expected theoretical values: approximately 46,000 daltons for the phosphatase, approximately 52,000 daltons for ea/phoA6 and approximately 47,000 daltons for Angio/phoA6. By prolonging the bacterial culture by 4 hours after labeling (chase), no degradation of the labeled proteins is observed. These results show that the phosphatase hybrid proteins do not undergo any proteolytic degradation during their production. This is by no means the case in respect of the hybrid proteins obtained by fusion of staphylococcus protein A or of E. coli β-galactosidase. In these systems, the majority of the expected hybrid protein undergoes a proteolytic degradation.

b. After 24 hours' incubation under the visualization conditions of the ELISA test, no significant fall in enzymatic activity of the hybrids is observed. This result demonstrates the stability of the reagent during use. In consequence, the visualization time of an ELISA test may be prolonged in order to increase its sensitivity.

c. After 10 cycles of freezing at −180° C. followed by thawing at 37° C., that is to say under drastic conditions, 95% of the phosphatase activity of the hybrids is preserved. Preliminary studies have yielded similar results in respect of lyophilization. It hence appears that the phosphatase hybrids can remain perfectly stable under normal conditions of packaging.

Example 6: Method for Screening cDNA or Genomic Libraries, According to the Invention.

The combined cloning and expression systems currently on the market are integrated in bacteriophages or plasmids.

Their essential common characteristics are as follows: they possess a portion of the lacZ gene of *E. coli* (β-galactosidase), modified in such a way that it contains one or, more often, a series of unique restriction sites. The insertion of DNA fragments of this site generally leads to loss of the β-galactosidase activity. This property makes it possible to recognize the recombinant clones, which form colorless colonies or lyric plaques, whereas the clones without an insert appear blue in the presence of X-Gal. Moreover, the inserted DNA sequences may be expressed in the form of fusion proteins with a fragment of the β-galactosidase. Their detection is then possible using antibodies specific for the desired proteins. The visualization is performed by different techniques: labeling with iodine[125] or the use of antibody-enzyme conjugates (Molecular Cloning, 1989, 12–14). Substitution in these systems of the modified lacZ gene by the modified phoA gene, in particular as described for plasmid pLIP1, leads to the appearance of blue and colorless clones in the presence of XP. In this case, the situation is the opposite of that occurring in the systems using β-galactosidase, the clones capable of converting the colorimetric substrate, XP in this instance, being recombinant clones. Furthermore, the simple coloration of a clone is indicative of several properties. It means that: i) a DNA fragment has been inserted into the phoA gene, ii) this fragment codes for an open reading frame, iii) the insertion has enabled the phoA gene to be shifted back into phase and to be expressed in the form of a hybrid protein, iv) this hybrid protein is exported into the periplasm and v) the recombinant alkaline phosphatase dimerizes to form an active enzyme which hydrolyzes its substrates, and in particular the colorimetric substrates. Thus, the information revealed by the colorimetric test is much more extensive than in the case of β-galactosidase. The use of the latter enzyme permits distinction between the clones with an insert and the clones without an insert without invoking the existence or the properties of a recombinant protein, whereas the use of alkaline phosphatase enables the clones capable of synthesizing an exportable hybrid protein possessing a structured and enzymatically active phoA domain to be identified directly. Moreover, the capacity of the hybrid proteins to be exported to the periplasm is not without an effect on the structuring of the polypeptide inserted into phoA. In the case of erabutoxin a, its exportation is accompanied by the formation of its disulfide bridges. It thus adopts a conformation enabling it to be recognized by antibodies specific for the structured form of the toxin. Most antibodies have this type of conformation-dependent specificity, and recognize only correctly structured proteins. Finally, it is possible to turn to good account the enzymatic activity of the hybrid proteins synthesized in order to demonstrate very simply an interaction with antibodies specific for the inserted protein. A simple blotting of the colonies synthesizing the recombinant proteins onto a nitrocellulose filter saturated beforehand with a solution of specific antibodies, followed by a visualization with a colorimetric reagent for the phosphatase, will enable the clones secreting a hybrid protein capable of reacting with the antibodies to be visualized.

This method can also prove extremely efficacious for identifying the epitopes of a defined protein. DNA fragments coding for this protein may be obtained by synthesis, by the action of restriction enzymes on the whole gene or by any other method such as the use of PCR (polymerase chain reaction) techniques, for example, and integrated in the phoA gene. A study of the interaction of the recombinant proteins resulting from these constructions with sera or monoclonal antibodies directed towards the whole protein then enables the regions of the protein bearing the epitopes to be identified.

Example 7: Method for the Selection of Recombinant Clones, According to the Invention.

The use of the bla gene which codes for β-lactamase, an enzyme which confers ampicillin resistance on the bacterium which expresses it, makes available a screen for selection of the recombinant clones which alone can grow in the presence of the antibiotic. This type of selection enables very rare coding sequences to be investigated.

As emerges from the foregoing, the invention is in no way limited to those methods of implementation, embodiments and methods of application which have just been described more explicitly; on the contrary, it encompasses all the variants which may occur to the practitioner in the field, without departing from the scope or the range of the present invention.

We claim:

1. A kit for carrying out an immunoenzymological assay for protein, comprising a diagnostic reagent consisting of a hybrid protein comprising, in order, a polypeptide P1 which is an N-terminal portion of mature alkaline phosphatase comprising from 6 to 28 of the N-terminal amino acids of said mature alkaline, joined to a polypeptide P2 capable of interacting with an antibody or an antigen, joined to a polypeptide P3 which is selected from the group consisting of a) the C-terminal remaining amino acids of said mature alkaline phosphatase, b) the mature sequence of alkaline phosphatase and c) enzymatically active fragments of b).

2. The kit of claim 1 wherein P1 contains amino acids 6 to 28 of the N-terminal amino acids of mature alkaline phosphatase.

3. The kit of claim 1 wherein P1 is the N-terminal portion of an alkaline phosphatase and P3 is the C-terminal remaining amino acids of said alkaline phosphatase.

4. The kit of claim 1 wherein said polypeptide P2 is erabutoxin or angiotensin I.

* * * * *